(12) United States Patent
Asai et al.

(10) Patent No.: US 10,814,117 B2
(45) Date of Patent: Oct. 27, 2020

(54) MICRONEEDLE SET

(71) Applicant: TOPPAN PRINTING CO., LTD., Taito-ku (JP)

(72) Inventors: Ryoichi Asai, Taito-ku (JP); Tomoya Sumida, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

(21) Appl. No.: 15/587,494

(22) Filed: May 5, 2017

(65) Prior Publication Data

US 2017/0239457 A1    Aug. 24, 2017

Related U.S. Application Data

(63) Continuation of application No. PCT/JP2015/005388, filed on Oct. 27, 2015.

(30) Foreign Application Priority Data

Nov. 5, 2014   (JP) ................... 2014-225377

(51) Int. Cl.
*A61M 37/00*   (2006.01)

(52) U.S. Cl.
CPC ... *A61M 37/0015* (2013.01); *A61M 2037/003* (2013.01); *A61M 2037/0023* (2013.01); *A61M 2037/0061* (2013.01); *A61M 2210/08* (2013.01)

(58) Field of Classification Search
CPC ...... A61M 37/0015; A61M 2037/0023; A61M 2037/003; A61M 2037/0061; A61M 2210/08

See application file for complete search history.

(56) References Cited

U.S. PATENT DOCUMENTS 5,009,652 A * 4/1991 Morgan .............. A61F 13/36
                                                604/378
7,347,835 B2   3/2008 Maenosono et al.
(Continued)

FOREIGN PATENT DOCUMENTS

JP   2005-021677 A   1/2005
JP   2005-304924 A   11/2005
(Continued)

OTHER PUBLICATIONS

International Search Report dated Dec. 22, 2015 in PCT/JP2015/005388, filed Oct. 27, 2015.

*Primary Examiner* — Jenna Zhang
(74) *Attorney, Agent, or Firm* — Oblon, McClelland, Maier & Neustadt, L.L.P.

(57) ABSTRACT

A microneedle set including a microneedle injection device that introduces a liquid to a skin of a body part, and a piercing assisting tool fixable to the body part. The microneedle injection device includes a hollow needle shaped body having a projection in an end portion thereof and a through hole connected to the projection such that the liquid passes through the through hole and is released from a tip portion of the projection, and a supply device that supplies the liquid to the hollow needle shaped body. The piercing assisting tool includes a fixing part which has an aperture formed therein and fixes a position of the aperture on the body part, and a cover connected to a peripheral portion of the aperture such that the aperture is opened or closed by the cover.

20 Claims, 9 Drawing Sheets

(56) References Cited

U.S. PATENT DOCUMENTS

| | | | | |
|---|---|---|---|---|
| 2003/0050602 A1* | 3/2003 | Pettis | ............... | A61M 5/46 604/117 |
| 2003/0187395 A1* | 10/2003 | Gabel | ............... | A61M 5/14248 604/134 |
| 2006/0127465 A1* | 6/2006 | Maenosono | ...... | A61M 37/0015 424/449 |
| 2008/0188779 A1* | 8/2008 | Vallero | ............... | A61N 1/0492 601/21 |
| 2008/0274166 A1* | 11/2008 | Sacks | ............... | A61K 9/7084 424/449 |
| 2009/0099502 A1* | 4/2009 | Tokumoto | ......... | A61M 37/0015 604/21 |
| 2009/0118662 A1* | 5/2009 | Schnall | ............... | A61N 1/303 604/20 |
| 2011/0251561 A1* | 10/2011 | Inou | ............... | A61M 37/0015 604/173 |
| 2012/0123387 A1* | 5/2012 | Gonzalez | ............ | A61M 5/2033 604/506 |
| 2014/0257190 A1* | 9/2014 | Yue | ............... | A61M 5/283 604/173 |
| 2015/0217101 A1* | 8/2015 | Sumida | ............. | A61M 37/0015 604/173 |
| 2016/0114144 A1* | 4/2016 | Sumida | ............. | A61M 37/0015 604/173 |

FOREIGN PATENT DOCUMENTS

| | | |
|---|---|---|
| JP | 2008-543359 A | 12/2008 |
| JP | 2010-46476 A | 3/2010 |
| JP | 4427691 B | 3/2010 |
| JP | 2012-95736 A | 5/2012 |
| JP | 5049268 B | 10/2012 |
| JP | 2013-500773 A | 1/2013 |
| JP | 5267910 B | 8/2013 |
| JP | 2014-004077 A | 1/2014 |
| WO | WO 2013136176 A1 * | 9/2013 ........ A61M 37/0015 |

* cited by examiner

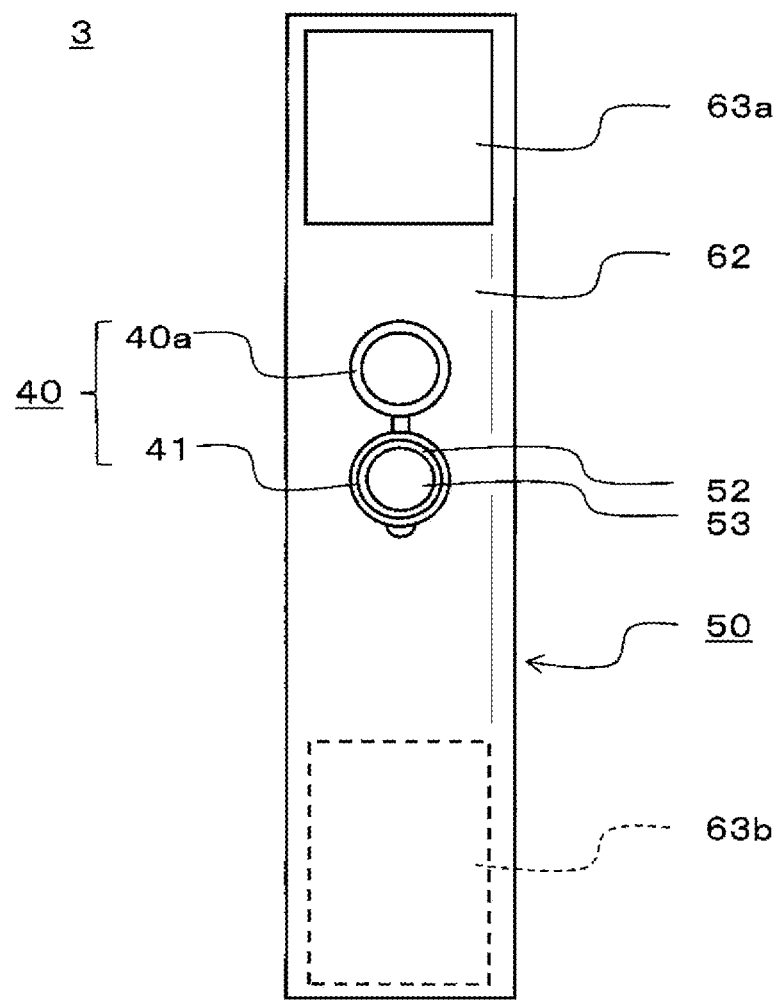

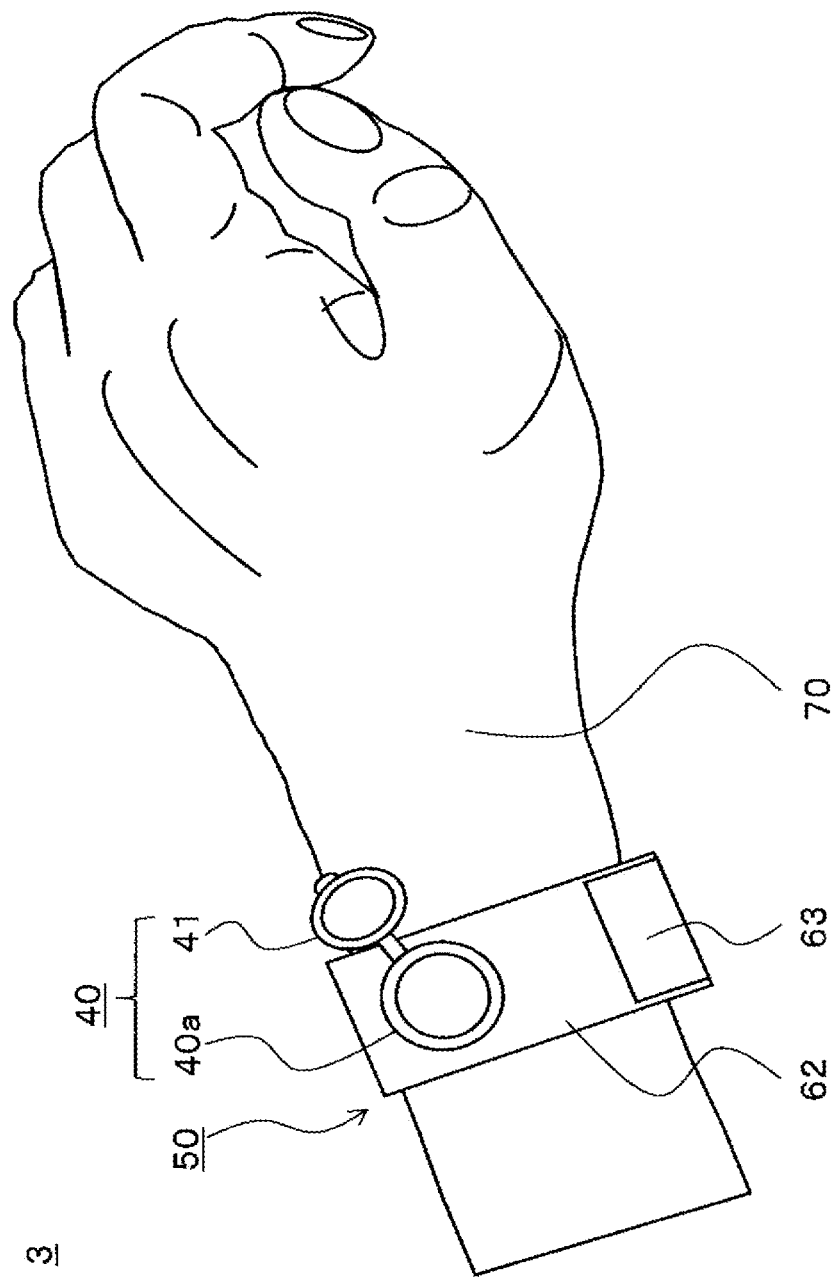

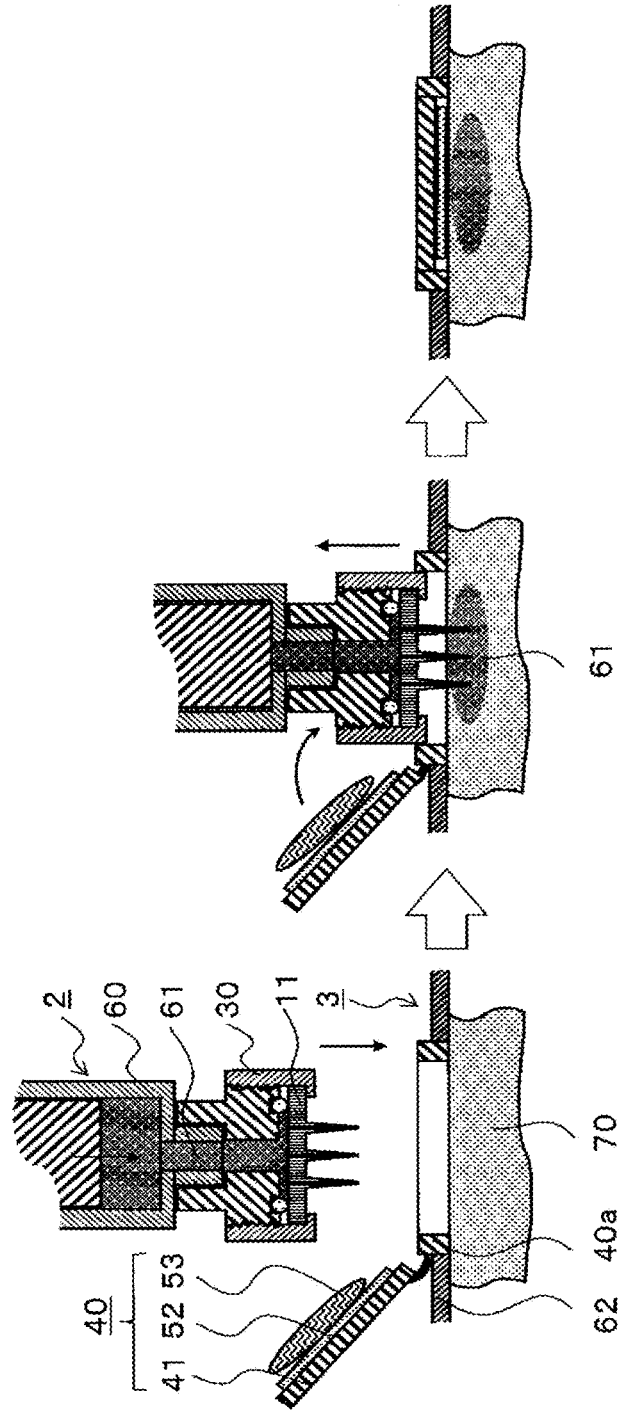

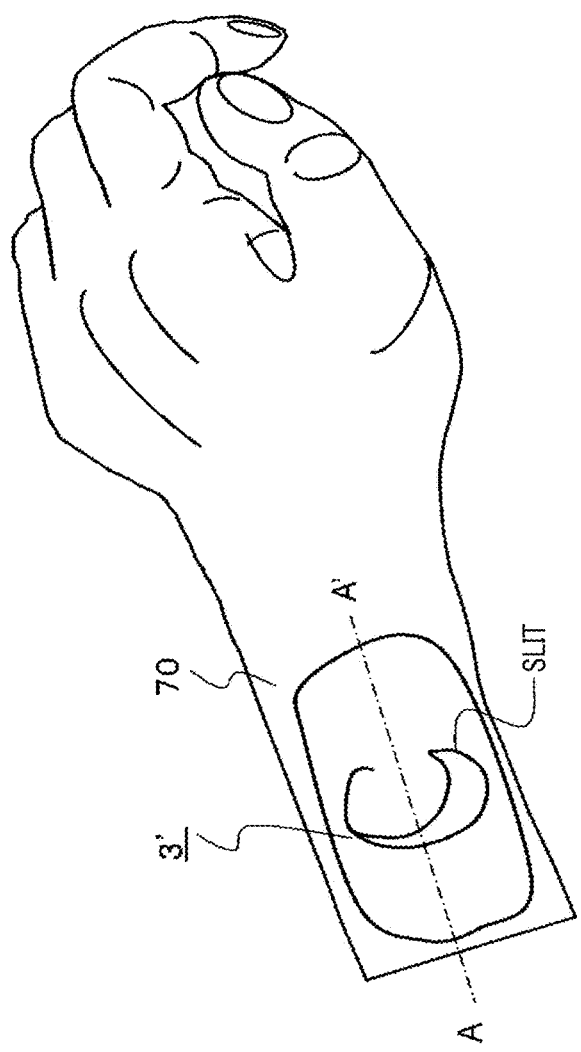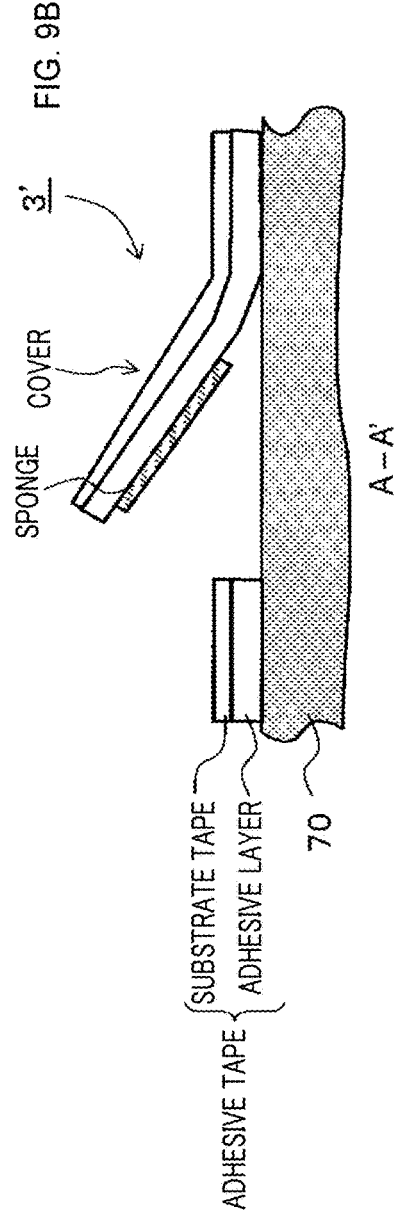

MICRONEEDLE SET

CROSS-REFERENCE TO RELATED APPLICATIONS

The present application is a continuation of International Application No. PCT/JP2015/005388, filed Oct. 27, 2015, which is based upon and claims the benefits of priority to Japanese Application No. 2014-225377, filed Nov. 5, 2014. The entire contents of these applications are incorporated herein by reference.

BACKGROUND OF THE INVENTION

Field of the Invention

The present invention relates to a microneedle set for percutaneous administration of vaccines or the like.

Discussion of the Background

Methods for administering a substance to be delivered into the body in a convenient manner without causing pain include percutaneous absorption, which allows a substance such as a drug to be delivered into the body by osmosis through the skin. In this method, a fine microneedle of the order of micrometers is used for piercing the skin to deliver a drug into the skin. The method is called microneedling. (See PTL 1).

A fine microneedle used for this technique preferably has a thinness and a tip angle sufficient for piercing the skin and a length sufficient for subcutaneous delivery of a drug solution. The diameter of the microneedle is preferably in the range from several micrometers to several hundreds of micrometers (specifically, approximately in the range from 1 μm to 300 μm) and the length is preferably from several tens of micrometers to several hundreds of micrometers (specifically, approximately in a range from 10 μm to 1000 μm).

Materials that constitute the microneedle are desired to be harmless to the body if the microneedle is left in the body. For example, biocompatible materials such as polylactic acid have been proposed (see PTL 2).

Microneedles are divided into solid types and hollow types. Solid types are divided into a coated type and a dissolving type. For microneedles of a coated type, a method of coating by immersion has been proposed as an example (see PTL 3). For microneedles of a dissolving type, a method of drying by dropping a biocompatible solution of water soluble material into a mold has been proposed as an example (see PTL 4). The hollow microneedle is a down-sized version of injection needles which are used for introducing a liquid to be injected into the body such as a drug solution or vaccine by using a conventional needle and a syringe.

Skills are required for inserting an injection needle into subcutaneous tissue in the body without any accompanying severe pain or major bleeding, as much as possible. Further, reuse of an injection needle may lead to various infections. Furthermore, workers in a waste treatment facility may be endangered, and people who had been injured by discarded injection needles have often suffered various infections.

In recent years, multi-needle shaped body devices having a plurality of needle shaped bodies of micron order formed on a plate-shaped support body have been used instead of conventional injection needles.

Since the length of the plurality of needle shaped bodies of micron order formed on a plate-like support body is made to be in the range of the thickness of intracutaneous tissue, the plurality of needle shaped bodies can be punctured into the intracutaneous tissue in the body without any accompanying pain or bleeding when the plurality of needle shaped bodies of micron order are pressed against the skin surface of the body.

The intracutaneous tissue is abundant in antigen-presenting cells. When a liquid to be injected into the body which acts on the antigen-presenting cells is introduced into the intracutaneous tissue, a smaller amount of such a liquid to be injected into the body can be used than required in the conventional case.

When such a hollow microneedle is used, the plurality of needle shaped bodies of the multi-needle shaped body device puncture into a site on the skin of the body where the liquid injected to the body is to be introduced so that the liquid injected to the body is introduced into the intracutaneous tissue in the body.

For example, a pad base for percutaneous drug administration has been proposed, in which a large number of fine needles are perpendicularly arranged on a skin-side surface of a sticking base material (see PTL 5). A large number of various fine needles have a tip-end portion which is horizontally truncated, and a bottomed hole for holding the drug from the horizontally truncated surface to near a base-end portion of a large number of various fine needles is formed.

This pad base is a portion responsible for percutaneous drug administration in a pad for percutaneous drug administration, and manufactured in a large quantity at low cost by injection molding or transfer molding such as imprinting or casting. Accordingly, the pad base becomes disposable, thereby reducing the risk of an infection caused by reuse. Since the large number of fine needles are small in length, and have tips which are horizontally truncated, and are formed on the pad base in a high density, people are less likely to be injured during disposal.

However, since this conventional pad base for percutaneous drug administration is designed to release a drug over a relatively long period of time, it is not suitable for introducing a precise desired amount of drug into the intracutaneous tissue in the body in a short period of time.

Further, a structure that is designed for introducing a drug into the intracutaneous tissue in the body in a short period of time by using a multi-needle shaped body device so as to introduce a predetermined amount of drug is disclosed (PTL 6).

In this structure, a plate spring having a first end fixed to a back surface of a substrate is provided to extend along the back surface of the substrate. A multi-needle shaped body device is mounted to the second end of the plate spring, and the plate spring is normally held elastically flexed such that the second end, that is, the position where the multi-needle shaped body device is attached is apart from the rear side of the base end. The first end of the plate spring is provided with a drug cartridge that stores a predetermined amount of drug, which is a liquid to be introduced in the body.

A surface of the substrate is brought into contact with a region on a skin surface of the body where the liquid is to be introduced followed by piercing the multi-needle shaped body into the region by using the elastic force of the plate spring. At the same time, the drug in the drug cartridge is supplied to the multi-needle shaped body device, and introduced into the intracutaneous tissue in the region of skin of the body.

PTL 1: JP-B-4427691
PTL 2: JP-B-5267910
PTL 3: JP-B-5049268
PTL 4: JP-A-2014-004077
PTL 5: JP-A-2005-021677
PTL 6: JP-A-2013-500773

SUMMARY OF THE INVENTION

According to an aspect of the present invention, a microneedle set includes a microneedle injection device that introduces a liquid to a skin of a body part and a piercing assisting tool fixable to the body part. The microneedle injection device includes a hollow needle shaped body having a projection in an end portion thereof and a through hole connected to the projection such that the liquid passes through the through hole and is released from a tip portion of the projection, and a supply device that supplies the liquid to the hollow needle shaped body. The piercing assisting tool includes a fixing part which has an aperture formed therein and fixes a position of the aperture on the body part, the aperture having an inner diameter equal to or larger than an outer diameter of the microneedle injection device, and a cover connected to a peripheral portion of the aperture such that the aperture is opened or closed by the cover.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 6 is a schematic view of a piercing assisting tool.

FIG. 7 is a schematic view which shows the piercing assisting tool in a state of use.

FIGS. 8A-8C are schematic cross-sectional views which show a procedure of piercing and drug solution introduction using the microneedle set.

FIGS. 9A and 9B are schematic views which show a modified example of the piercing assisting tool.

DESCRIPTION OF THE EMBODIMENTS

Figure 1:
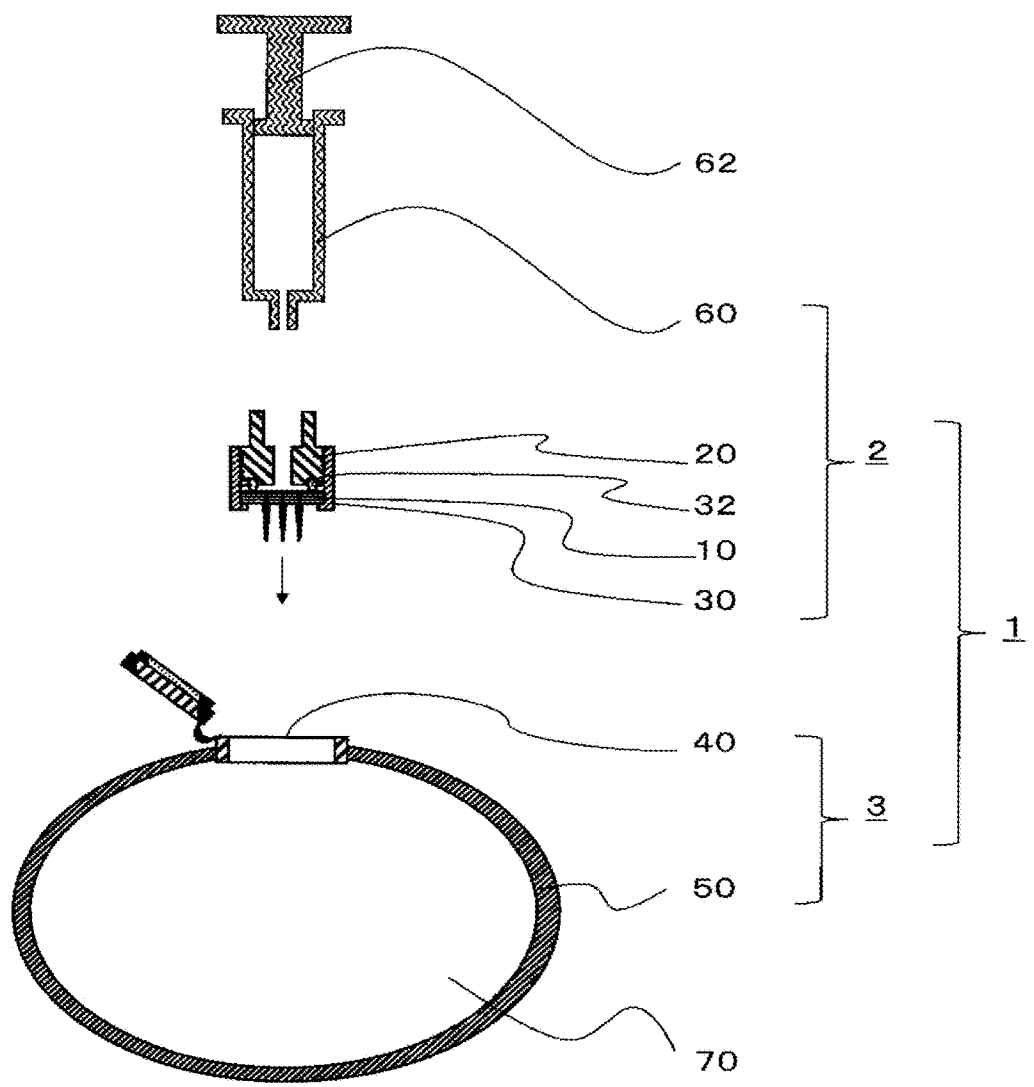
FIG. 1 is a schematic cross-sectional view of a microneedle set according to an embodiment of the present invention.

The embodiments will now be described with reference to the accompanying drawings, wherein like reference numerals designate corresponding or identical elements throughout the various drawings.

With reference to the drawings, a microneedle set 1 according to an embodiment of the present invention will be described. FIG. 1 is a schematic cross-sectional view of the microneedle set 1.

As shown in FIG. 1, the microneedle set 1 includes a microneedle injection device 2 and a piercing assisting tool 3 fixed to a limb 70. The microneedle injection device 2 is made up of, as an example, a hollow needle shaped body device 10, a syringe supporting section 20, a hollow needle shaped body supporting section 30, a liquid sealing member (O ring) 32 and a syringe 60 which is a drug solution supply means. A piercing assisting tool 3 is made up of, as an example, a piercing assisting member 40 and a belt-like fixing tool 50. It is assumed that the piercing assisting tool 3 is fixed to the limb 70 before introducing a drug solution into the skin by using the microneedle injection device 2.

The inventors have found that a microneedle injection device including a hollow needle shaped body for subcutaneous injection should be structured for immediate protection of a skin surface after a drug solution is introduced. In subcutaneous injection, the skin surface should be immediately protected since the skin surface may swell right after drug solution introduction compared with intracutaneous injection. The inventors have devised a microneedle set made up of a combination of a piercing assisting tool capable of being fixed to a skin in advance before piercing introduction by the microneedle injection device to protect a skin surface immediately after a drug solution is introduced, and a microneedle injection device.

Of course, a microneedle set of the present invention is not limited to this embodiment, and may be appropriately modified.

Figure 2:
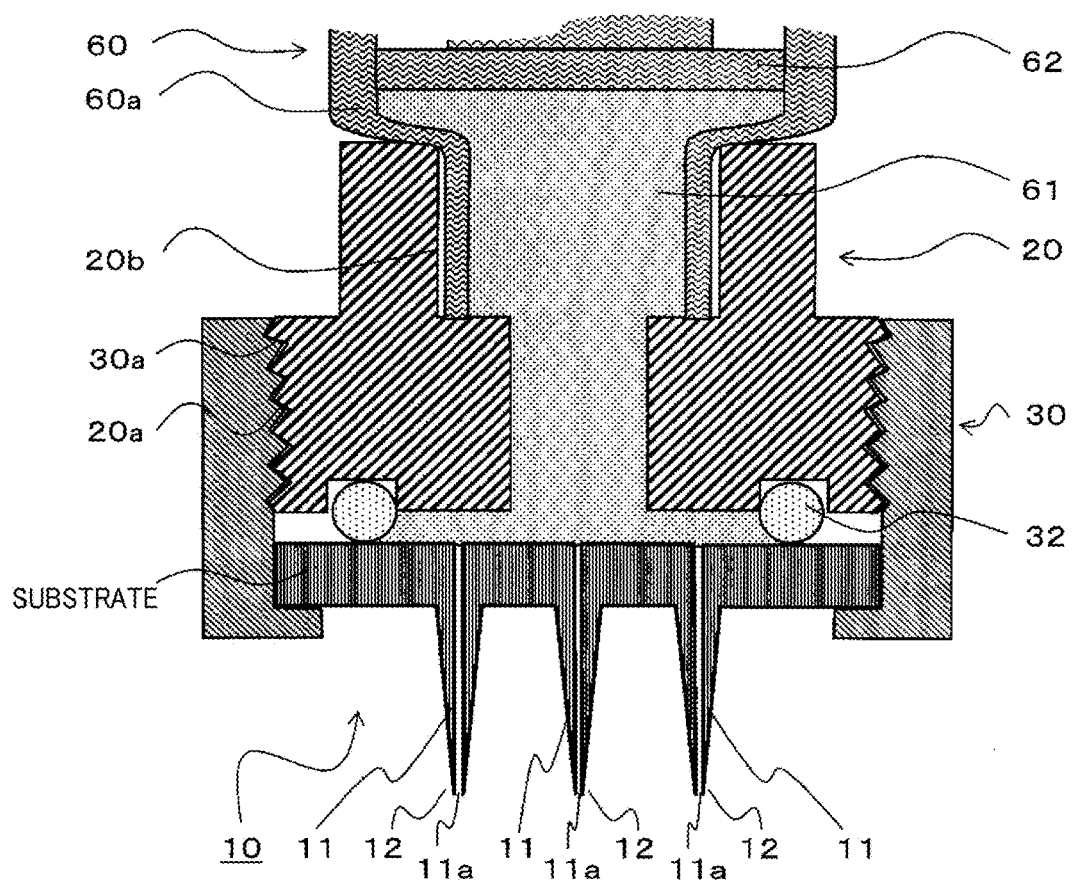
FIG. 2 is a cross sectional view of a microneedle injection device.
Figure 3B:
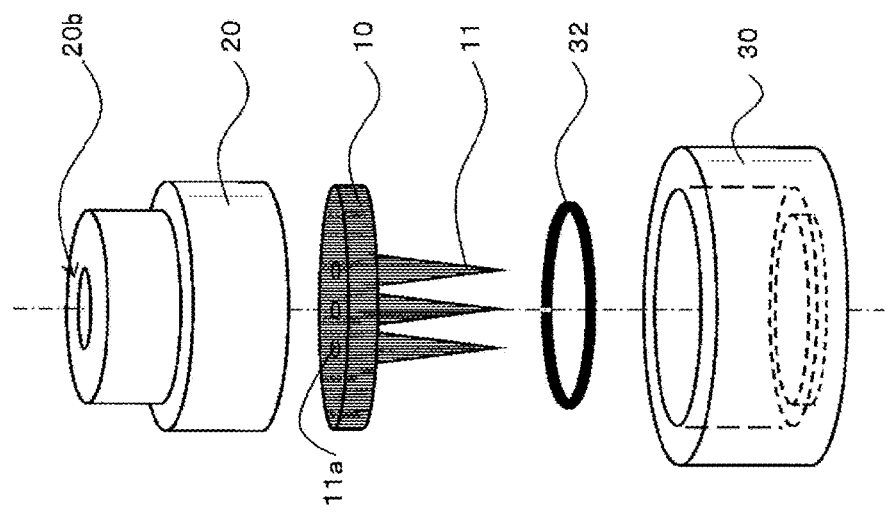
FIGS. 3A and 3B are a perspective view and an exploded view of the microneedle injection device.
Figure 3A:
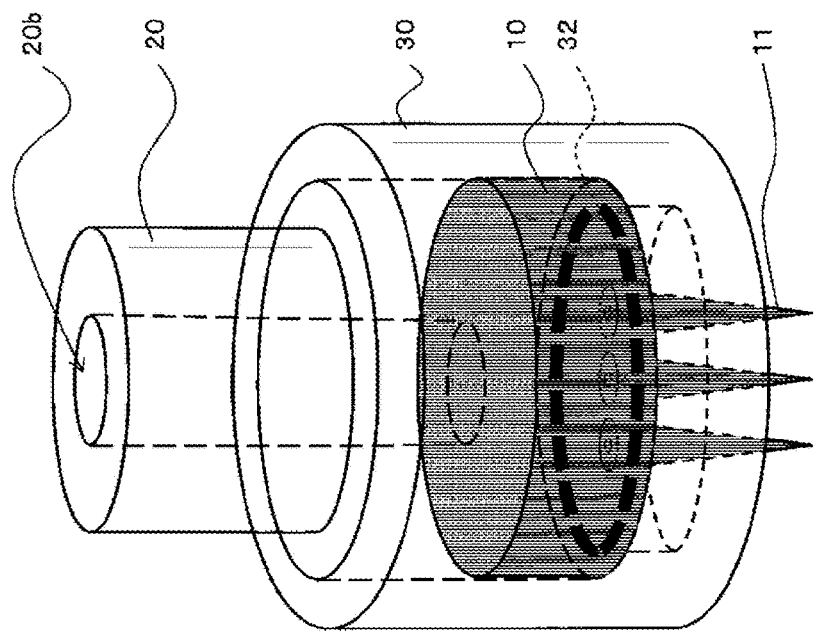

With reference to FIGS. 2-3B, elements of the microneedle injection device 2 will be described. FIG. 2 shows a cross-sectional view of the microneedle injection device 2. FIGS. 3A and 3B show a perspective view and an exploded view of the microneedle injection device 2 which does not have the syringe 60. An external thread 20a and an internal thread 30a, which will be described later, are not shown in FIGS. 3A and 3B.

<Syringe>

The syringe 60 stores a drug solution 61, and the drug solution 61 is supplied to a hollow needle shaped body 11, which is described later, when a piston 62 is inserted into the syringe 60. The syringe 60 includes an external cylinder 60a which is substantially transparent such that users can visually recognize an amount of the drug solution 61 held in the syringe 60 from outside. Further, the external cylinder 60a has a scale on an outer surface thereof to clearly show an amount of the drug solution 61. Hence, a precise desired amount of drug solution 61 is introduced into the intracutaneous tissue in a short period of time.

<Hollow Needle Shaped Body Device>

The hollow needle shaped body device 10 is provided with the hollow needle shaped body 11 on a first surface of a disk which serves as a substrate. The hollow needle shaped body 11 is not provided on a surface which is opposite to the first surface (hereinafter, referred to as a second surface). The hollow needle shaped body 11 has a projection 12 at the tip end and a through hole 11a which communicates the projection 12 with the second surface so that the drug solution 61 is released through the second surface. In the hollow needle shaped body device 10, at least one hollow needle shaped body 11 is provided. Preferably, a plurality of hollow needle shaped bodies 11 are provided.

In manufacturing of the hollow needle shaped body device 10, a non-through hole is first formed on the substrate. Here, a step of forming the non-through hole can be performed by various known techniques such as wet etching, dry etching, laser processing, machining and the like. Then, an etching mask is formed on a surface of the substrate which is opposite to a surface where the non-through hole is formed. Here, the etching mask has a shape which includes a circular arc on a part of or entirety of the outer shape of a bottom portion and has a thickness continuously increasing from a peripheral portion to a center portion. In a step of forming the etching mask, the etching mask is aligned with an earlier formed non-through hole. Then, etching is performed by using the etching mask to form a needle shaped structure on the substrate. In this structure, the earlier formed non-through hole may or may not be a through hole. Then, an upper inclined surface is provided on the structure to thereby form the hollow needle shaped body 11 having the through hole 11a.

A material for the hollow needle shaped body device 10 may be any material capable of being processed by wet etching, dry etching or the like. For example, the material may include metal such as titanium, aluminum or stainless steel, synthetic resin such as polycarbonate, polystyrene, acrylic resin or fluorine resin, or silicon.

In the hollow needle shaped body device 10, the hollow needle shaped body 11 is formed of a biocompatible material. The entire hollow needle shaped body device 10 is preferably integrally formed of the biocompatible material. A known biocompatible material is, for example, metal materials such as stainless steel, titanium or manganese, resin materials such as silicone for medical applications, polyglycolic acid or polycarbonate, and inorganic materials such as silicon. However, a forming material for the hollow needle shaped body device 10 is not limited to these materials.

When the entire hollow needle shaped body device 10 including the hollow needle shaped body 11 is integrally formed of the biocompatible material, conventional molding techniques, for example, such as injection molding, extrusion molding, imprinting, hot embossing or casting can be used. In the plurality of hollow needle shaped bodies 11, the through hole 11a is formed toward a projection 12 of the hollow needle shaped body 11 from the second surface of the hollow needle shaped body device 10 along the center line of the projection 12 by conventional micro drilling techniques such as micro drilling or laser drilling. The through hole 11a may or may not be concentric with the center of the hollow needle shaped body 11.

The shape of the plurality of hollow needle shaped bodies 11 may be, for example, a polygonal pyramid including a conical pyramid, a triangular pyramid and a quadrangular pyramid, a cylinder or a polygonal column. The height from the first surface of the hollow needle shaped body device 10 is set in the range of the thickness of the intracutaneous tissue of a living body which may be a human.

<Syringe Supporting Section and Hollow Needle Shaped Body Supporting Section>

The syringe supporting section 20 is provided with an opening having the external thread 20a on the outer periphery and an opening 20b which is connected to the syringe 60. It is preferable that the opening 20b for connecting the syringe 60 is tapered in conformity with the Luer-Lock standard, and a projection for attachment of an injection needle is provided at a tip of the external cylinder 60a of the syringe 60, so that the syringe supporting section 20 is connected to the syringe 60 in a liquid-tight manner.

The external thread 20a is screwed to the internal thread 30a formed on the hollow needle shaped body supporting section 30, and sandwiches an O ring 32 to configure a liquid-tight structure in which the hollow needle shaped body device 10 is removably fixed. The liquid-tight structure is provided by an annular liquid-tight member, for example, the O ring 32, which is sandwiched between the syringe supporting section 20 and the hollow needle shaped body device 10, for example. In this embodiment, a portion which is in contact with the drug solution 61 needs to be covered by or formed of a substance which does not degrade the drug solution 61, or is not degraded by the drug solution 61. The O ring 32 which is the liquid-tight member surrounds all the openings of the through holes 11a on the second surface of the hollow needle shaped body device 10.

A material for the syringe supporting section 20 and the hollow needle shaped body supporting section 30 is not specifically limited. However the material may include, for example, polyester such as polylactic acid, polyvinyl chloride, polyethylene, polypropylene, a cyclic polyolefin, polystyrene, poly-(4-methylpentene-1), polycarbonate, acrylic resin, acrylonitrile-butadiene-styrene copolymer, polyethylene terephthalate or polyethylene naphthalate, or resin such as butadiene-styrene copolymer or polyamide (for example, nylon 6, nylon 6-6, nylon 6-10 and nylon 12). Further, the syringe supporting section 20 and the hollow needle shaped body supporting section 30 are preferably transparent or translucent in order to secure interior visibility in case a solution leaks.

An exposed height H of the hollow needle shaped body is preferably in the range of 0.2 mm or more and 2 mm or less. The microneedle set 1 is highly effective for subcutaneous injection by the hollow needle shaped body 11 with the height H of 2 mm or less. Further, the exposed height H of the hollow needle shaped body 11 is defined as the length of the projection of a portion exposed from a peripheral member of the hollow needle shaped body 11. In the hollow needle shaped body 11 shown in FIG. 2, the exposed height H is defined as the length of a portion exposed from a reference surface of the hollow needle shaped body supporting section 30.

<Modified Examples of Microneedle Injection Device>

Figure 4:
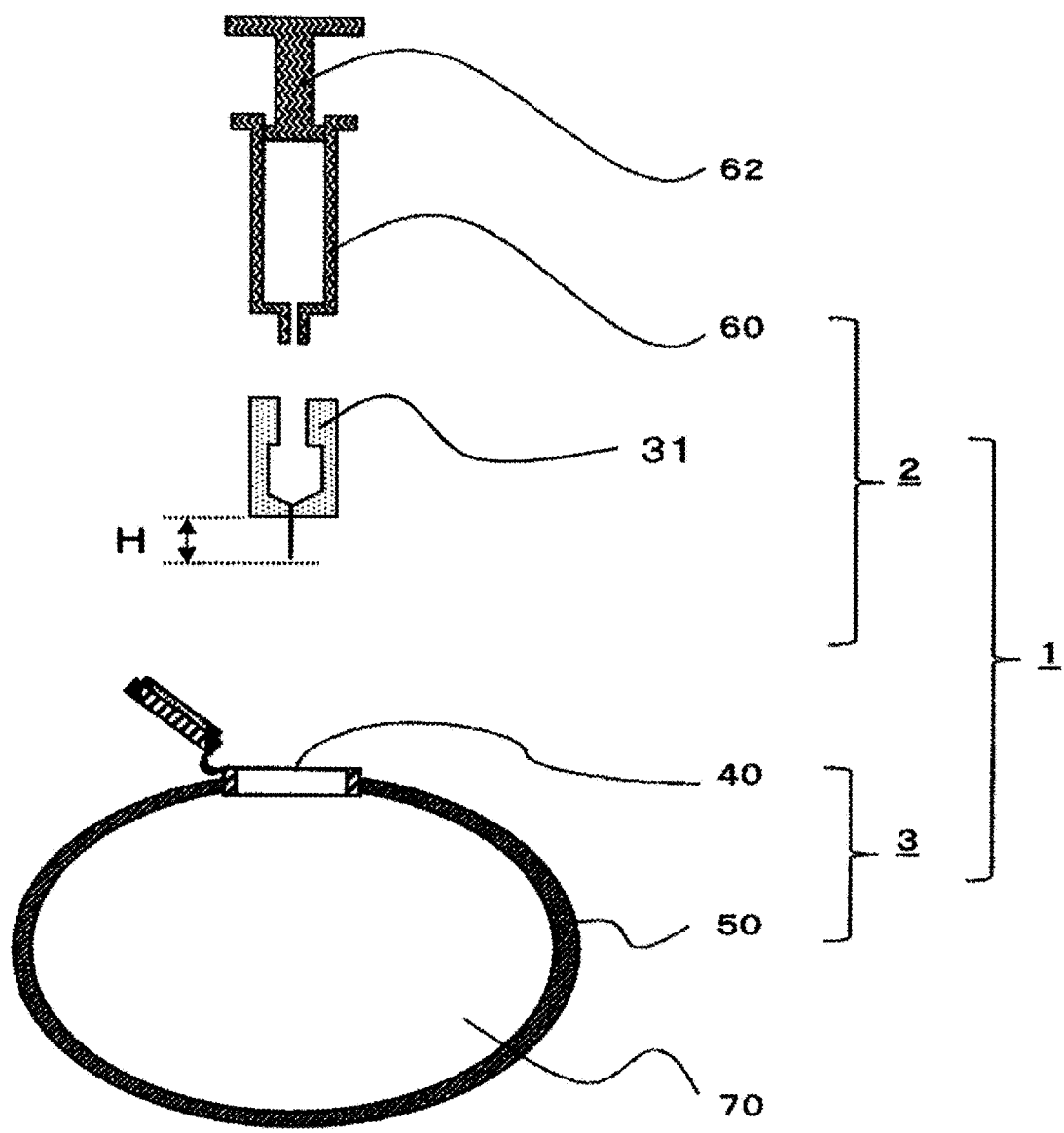
FIG. 4 is a schematic cross-sectional view of a microneedle set according to a modified example.

FIG. 4 shows a schematic cross-sectional view of a microneedle set according to a modified example of the present invention. The modified example of the microneedle injection device shown in FIG. 4 is provided with the syringe 60 which is the drug solution supply means, and the hollow needle structure 31 connected to the syringe 60. The hollow needle structure 31 is provided with a projection having a through hole with an exposed height H, and a drug solution supplied from the syringe 60 is released from the through hole. The hollow needle structure 31 is manufactured by injection molding or the like.

Figure 5:
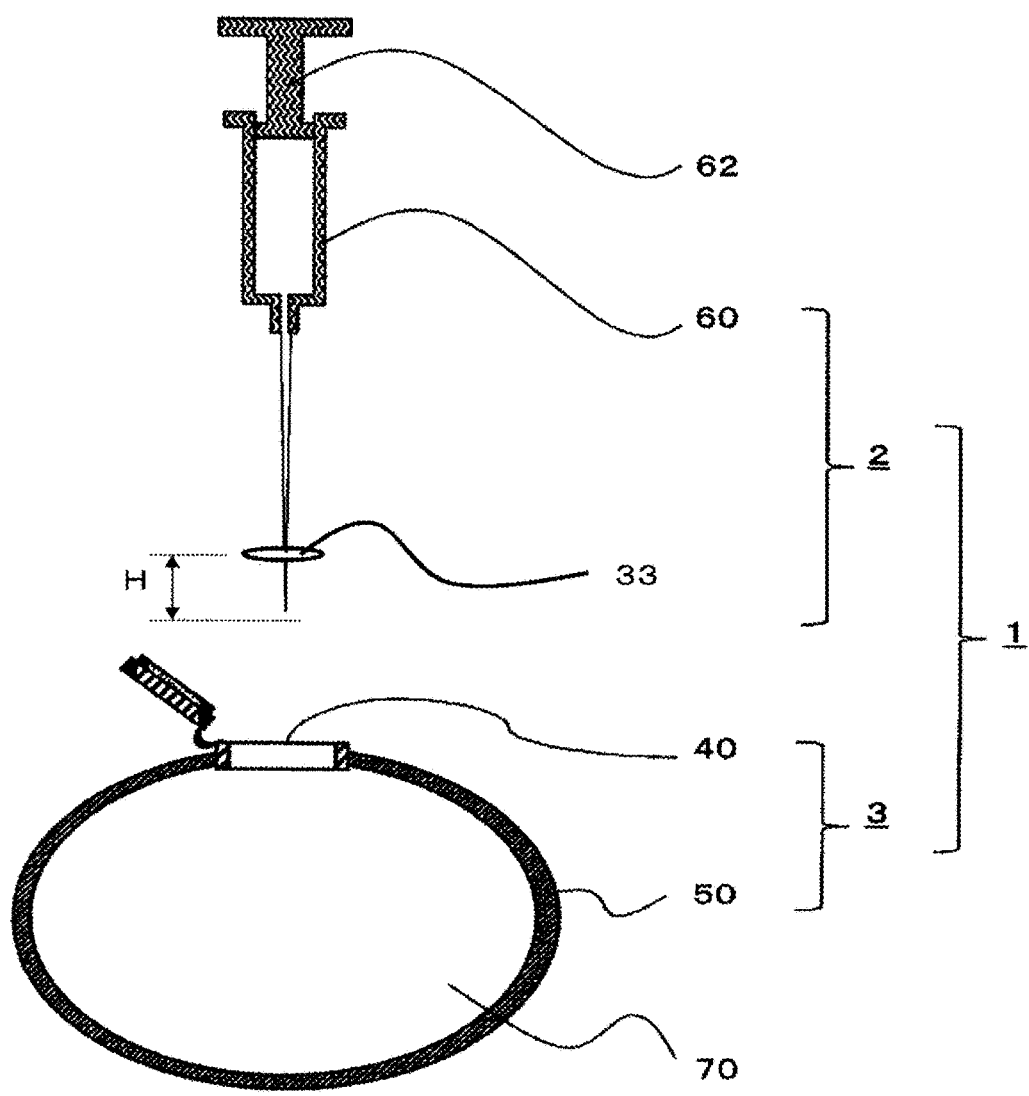
FIG. 5 is a schematic cross-sectional view of a microneedle set according to another modified example.

FIG. 5 shows a schematic cross-sectional view of a microneedle set according to another modified example of the present invention. In another modified example of the microneedle injection device shown in FIG. 5, the syringe 60 which is the drug solution supply means is connected to a needle, and a piercing depth control jig 33 is provided at a periphery of the needle. The piercing depth control jig 33 is fixed to the needle to control a piercing depth of the needle into the skin. Here, the length of the needle exposed from the piercing depth control jig 33 serves as the exposed height H.

<Piercing Assisting Tool>

FIG. 6 is a schematic view of the piercing assisting tool 3. FIG. 7 is a schematic view which shows the piercing assisting tool 3 in a state of use. The piercing assisting tool 3 includes the belt-like fixing tool 50 as the fixing section for fixing the piercing assisting member 40 to the limb. The piercing assisting member 40 is attached to the belt-like fixing tool 50, and is provided with an opening 40a formed such that an inner diameter thereof is to be equal to or larger than an outer diameter of the hollow needle shaped body supporting section 30. The piercing assisting member 40 is fixed to the belt-like fixing tool 50, which is described later, to be integrated together.

A cover 41 fixed to a periphery of the opening 40a to open and close the opening 40a is provided with a member 52 and a liquid absorbing member 53. The member 52 applies a pressure to a piercing mark by being integrated with the cover 41 in order to prevent leakage of the drug solution 61 from the piercing mark after piercing, that is, after the drug solution 61 has been introduced (injected) into the limb 70, and the hollow needle shaped body device 10 has been removed from the skin. The liquid absorbing member 53 is formed of a foam in a sponge-like shape or the like. The cover 41 is fixed to a periphery of the opening 40a. Accordingly, a part where the drug solution is introduced can immediately be protected with the cover after the drug solution introduction by the microneedle injection device.

The liquid absorbing member 53 preferably has swelling percentages for absorbed liquid of 100% or more, and is preferably formed of a sponge having a dry thickness of 0.5 mm or more before being used.

The liquid absorbing member 53 absorbs leaked drug solution 61. As a result, the liquid absorbing member 53 is thickened, and the volume thereof increases to some degree by swelling to achieve an appropriate pressing force. To achieve better performance, the liquid absorbing member 53 preferably has swelling percentages for absorbed liquid of 300% or more, and more preferably has a dry thickness of 0.8 mm or more before being used. A desired material of the sponge is a substance which has bioaffinity, and a cellulose sponge is preferable because of its easy availability. Further, the liquid absorbing member can be a gauze, a nonwoven fabric or the like.

<Belt-Like Fixing Tool>

The belt-like fixing tool 50, which serves as the fixing section to fix the piercing assisting member 40 to the limb 70, is provided with a belt 62 wound to the limb 70 which is to be pierced, and a fixing member 63 for fixing the belt 62 in the state of being wound onto the limb 70.

The belt 62 is a belt-like member having flexibility. The belt 62 is mounted so as to be wound around an outer perimeter of the limb 70 such as wrist or arm with both ends thereof overlapping each other.

A constituent material of the belt 62 is not specifically limited, but is preferably a material in which the site to be pierced can be visually recognized. For example, the constituent material may include a polyolefin such as polyvinyl chloride, polyethylene, polypropylene, polybutadiene or ethylene-vinyl acetate copolymers (EVA), polyester such as polyethylene terephthalate (PET) or polybutylene terephthalate (PBT), or various thermoplastic elastomers such as polyvinylidene chloride, silicone, polyurethane, polyamide elastomer, polyurethane elastomer, or polyester elastomer. Further, the belt 62 is preferably substantially transparent. Accordingly, the user can achieve reliable visual recognition of the site to be pierced. As a result, if the hollow needle shaped body device 10 pierced a site deviated from the site to be pierced, the user can easily recognize the deviation.

The belt 62 is provided with a male part of hook-and-loop fastener 63a and a female part of a hook-and-loop fastener 63b, generally called magic tape (registered trademark) or the like, as the fixing member 63 on the inner and outer surfaces of its end. As shown in FIG. 7, the male part of hook-and-loop fastener 63a engages with the female part of the hook-and-loop fastener 63b. As a result, the belt 62 is mounted to wrist (limb 70). Further, the fixing member 63 for fixing the belt 62 in the state of being wound around the wrist (limb 70) is not limited to the hook-and-loop fastener.

For example, the fixing member may be a snap, a button, a clip or a frame member through which an end of the belt 61 can pass.

FIGS. 8A-8C show a schematic cross-sectional view which shows a procedure of piercing and drug solution introduction using the microneedle set 1. First, the piercing assisting tool 3 is fixed to the limb 70, and then, the microneedle injection device 2 in which the syringe 60 is filled with the drug solution 61 is prepared. At this time, as shown in FIG. 8A, the cover 41 to which the liquid absorbing member 53 is attached is open. Then, the limb 70 is pierced with the hollow needle shaped body 11 of the microneedle injection device 2. At this time, as shown in FIG. 8B, the hollow needle shaped body 11 is pierced into the body while an outer periphery of the hollow needle shaped body supporting section 30 is fitted into an inner periphery of the piercing assisting member 40. After the hollow needle shaped body 11 is pierced into the body, the drug solution 61 is introduced. After the drug solution 61 is introduced, as shown in FIG. 8C, the microneedle injection device 2 is removed, and the cover 41 is closed to cover a pierced portion with the liquid absorbing member 53 and the cover 51. With this piercing procedure, the hollow needle shaped body 11 is safely and accurately pierced into the limb 70. Further, the liquid absorbing member 53 can reliably keep pressing the piercing mark by being pressed by the cover 41 without being disengaged due to an external shock. Further, properties of the liquid absorbing member 53 can distribute a pressure to reduce unpleasant pain.

FIGS. 9A and 9B show a schematic view and a schematic cross-sectional view showing a piercing assisting tool 3' in a state of use which is a modified example of the piercing assisting tool 3. In the piercing assisting tool 3', instead of the belt-like fixing tool 50, an adhesive tape for the limb in which an adhesive layer is laminated to a substrate tape is used. In the center of the adhesive tape, there is a slit to form an opening of a size in which an outer diameter of the microneedle injection device can fit. A region defined by the slit of the adhesive tape serves as a cover by which a part of the adhesive tape can be opened or closed, and the absorbing member such as the sponge can be provided to a back surface of the adhesive layer of the cover. Further, the piercing assisting tool 3' shown in FIGS. 9A and 9B is also applied to the microneedle injection device shown in FIGS. 4 and 5.

In a hollow microneedle, a liquid drug (drug solution) is introduced into a position near a skin surface. After piercing and introduction of the drug by using the hollow microneedle, the skin surface swells. In such a swollen skin surface after the piercing and drug introduction, a part of the introduced drug solution may leak due to a subsequent contact, shock or the like to the skin surface. A drug solution leaking after piercing introduction may impart an unpleasant impression to users. Accordingly, an aspect of the present invention is to provide a microneedle set capable of preventing leakage of the drug solution from a skin surface which is swollen after piercing injection or capable of wiping a drug solution leaked from the skin surface which is swollen after piercing introduction.

An aspect of the present invention to solve the problems is a microneedle set including a microneedle injection device including a hollow needle shaped body which has a projection at a tip end, and is provided with a through hole that allows for a drug solution to be released from a tip of the projection, and a drug solution supply means that is connected to the hollow needle shaped body so as to supply the drug solution to be released from the tip of the projection, and a piercing assisting tool including an aperture having an inner diameter equal to or larger than an outer diameter of the microneedle injection device, a cover connected to a periphery of the aperture and capable of opening and closing the aperture, and a fixing section for fixing the aperture to a limb.

As the fixing section of the piercing assisting tool, a belt-like fixing tool capable of being wound around the limb may further be included.

As the fixing section of the piercing assisting tool, an adhesive tape capable of being adhered to the limb may further be included.

The adhesive tape may include a slit, and a region defined by the slit on the adhesive tape may be a cover.

The cover may further include a liquid absorbing member on a face which is to be in contact with the limb.

In the microneedle injection device, an exposed height H of the projection may be in the range of 0.2 mm or more and 2 mm or less.

A microneedle set according to an embodiment of the present invention can protect a pierced part immediately and accurately after a drug solution is introduced into the limb by a microneedle injection device, and preventing drug solution leaking from a skin surface which is swollen after piercing introduction. Alternatively, the microneedle set can wipe the drug solution leaked from the skin surface which is swollen after piercing injection.

Industrial Applicability

As described above, contaminants caused by an introduction of a drug solution can be prevented. Further, availability in a clinical medical field is extremely high since quick and painless percutaneous drug administration can be achieved by a simple press operation when in use. Moreover, besides the medical field, availability also exists in drug discovery, cosmetics, beauty applications or the like.

REFERENCE SIGNS LIST

1: Microneedle set
2: Microneedle injection device
3: Piercing assisting tool
10: Hollow needle shaped body device
11: Hollow needle shaped body
11a: Through hole
12: Projection
20: Syringe supporting section
20a: External thread
20b: Opening
30: Hollow needle shaped body supporting section
30a: Internal thread
31: Hollow needle
32: O ring
33: Piercing depth control jig
40: Piercing assisting member
40a: Opening
41: Cover
50: Belt-like fixing tool
52: Member
53: Absorbing member (foam)
60: Syringe
60a: External cylinder
61: Drug solution
62: Belt
63: Fixing member
62a: Hook-and-loop fastener (male part)
62a: Hook-and-loop fastener (female part)
70: Limb Obviously, numerous modifications and variations of the present invention are possible in light of the above teachings. It is therefore to be understood that within the scope of the appended claims, the invention may be practiced otherwise than as specifically described herein.

What is claimed is:

1. A microneedle set, comprising:
a microneedle injection device configured to introduce a liquid to a skin of a body part; and
a piercing assisting tool having an aperture, configured to fix a position of the aperture on the body part, and including a cover connected to a peripheral portion of the aperture such that the cover opens and closes the aperture,
wherein the microneedle injection device includes a hollow needle shaped body comprising a substrate and a projection formed on a surface of the substrate, a hollow needle shaped body supporting section having a hollow space that supports the substrate of the hollow needle shaped body such that the projection of the hollow needle shaped body projects outside the hollow space of the hollow needle shaped body supporting section, a syringe supporting section that engages with the hollow needle shaped body supporting section and supplies the liquid to the hollow needle shaped section such that the syringe supporting section is positioned inside the hollow space of the hollow needle shaped body supporting section and that the liquid is released from a tip portion of the projection into the body part at the position of the aperture, and a syringe configured to engage with the syringe supporting section and supply the liquid to the hollow needle shaped body through the syringe supporting section, the piercing assisting tool is formed such that the aperture is configured to receive the microneedle injection device and has an inner diameter equal to or larger than an outer diameter of the microneedle injection device, the hollow needle shaped body supporting section has an internal thread portion formed inside the hollow space, and the syringe supporting section has an external thread portion configured to engage with the internal thread portion of the hollow needle shaped body supporting section such that the syringe supporting section is positioned inside the hollow space of the hollow needle shaped body supporting section, and the cover of the piercing assisting tool comprises a liquid absorbing member that absorbs the liquid and positioned to make contact with the body part when the cover closes the aperture.

2. The microneedle set of claim 1, wherein the body part is a limb, and the piercing assisting tool comprises a belt-like fixing tool configured to be placed around the limb.

3. The microneedle set of claim 2, wherein the liquid absorbing member of the cover has a swelling percentage of 100% or more for the liquid.

4. The microneedle set of claim 2, wherein the projection has an exposed height H in a range of from 0.2 mm to 2 mm.

5. The microneedle set of claim 2, wherein the microneedle injection device has a liquid sealing member sandwiched between the hollow needle shaped body and the syringe supporting section inside the hollow needle shaped body supporting section.

6. The microneedle set of claim 1, wherein the piercing assisting tool comprises an adhesive tape that adheres to the body part.

7. The microneedle set of claim 6, wherein the adhesive tape has a slit formed such that the cover comprises a portion of the adhesive tape cut out by the slit.

8. The microneedle set of claim 7, wherein the liquid absorbing member of the cover has a swelling percentage of 100% or more for the liquid.

9. The microneedle set of claim 6, wherein the liquid absorbing member of the cover has a swelling percentage of 100% or more for the liquid.

10. The microneedle set of claim 6, wherein the projection has an exposed height H in a range of from 0.2 mm to 2 mm.

11. The microneedle set of claim 1, wherein the liquid absorbing member of the cover has a swelling percentage of 100% or more for the liquid.

12. The microneedle set of claim 11, wherein the projection has an exposed height H in a range of from 0.2 mm to 2 mm.

13. The microneedle set of claim 11, wherein the liquid absorbing member of the cover is a sponge having a dry thickness of 0.5 mm or more before use.

14. The microneedle set of claim 1, wherein the projection has an exposed height H in a range of from 0.2 mm to 2 mm.

15. The microneedle set of claim 1, wherein the liquid absorbing member of the cover is a sponge.

16. The microneedle set of claim 1, wherein the liquid absorbing member of the cover is a sponge having a dry thickness of 0.5 mm or more before use.

17. The microneedle set of claim 1, wherein the liquid absorbing member of the cover is a cellulose sponge.

18. The microneedle set of claim 1, wherein the liquid absorbing member of the cover is a gauze or a nonwoven fabric.

19. The microneedle set of claim 1, wherein the projection of the hollow needle shaped body in the microneedle injection device has a piercing depth control jig at an exposed height H in a range of from 0.2 mm to 2 mm.

20. The microneedle set of claim 1, wherein the microneedle injection device has a liquid sealing member sandwiched between the hollow needle shaped body and the syringe supporting section inside the hollow needle shaped body supporting section.

* * * * *